(12) United States Patent
Chong et al.

(10) Patent No.: US 8,512,289 B2
(45) Date of Patent: Aug. 20, 2013

(54) RESERVOIR FILLING SYSTEMS AND METHODS

(75) Inventors: Colin A. Chong, Burbank, CA (US);
Truong Gia Luan, Winnetka, CA (US);
Rafael Bikovsky, Oak Park, CA (US);
Arsen Ibranyan, Glendale, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 101 days.

(21) Appl. No.: 13/348,585

(22) Filed: Jan. 11, 2012

(65) Prior Publication Data

US 2012/0116302 A1 May 10, 2012

Related U.S. Application Data

(62) Division of application No. 12/499,283, filed on Jul. 8, 2009, now Pat. No. 8,167,846.

(51) Int. Cl.
*A61M 1/00* (2006.01)

(52) U.S. Cl.
USPC .......................................... 604/152; 604/228

(58) Field of Classification Search
CPC ....................................................... A61M 1/00
USPC ........ 29/428; 137/565.17; 141/2; 604/151, 604/152, 218, 228
See application file for complete search history.

(56) References Cited

U.S. PATENT DOCUMENTS

| | | | |
|---|---|---|---|
| 3,640,437 A | 2/1972 | Galy | |
| 4,150,672 A | 4/1979 | Whitney et al. | |
| 4,648,872 A | 3/1987 | Kamen | |
| 5,980,489 A | 11/1999 | Kriesel | |
| 6,045,533 A * | 4/2000 | Kriesel et al. | 604/132 |
| 2002/0128595 A1 | 9/2002 | Weston et al. | |
| 2003/0100866 A1 | 5/2003 | Reynolds | |

(Continued)

FOREIGN PATENT DOCUMENTS

| | | |
|---|---|---|
| AU | 5391773 A | 10/1974 |
| EP | 1 488 818 A1 | 12/2004 |
| WO | WO-03/089029 A1 | 10/2003 |
| WO | WO-03/099357 A1 | 12/2003 |
| WO | WO-2008/103175 A1 | 8/2008 |
| WO | WO-2009/12659 A2 | 10/2009 |

OTHER PUBLICATIONS

Partial search report dated Nov. 8, 2010 from related patent application No. PCT/U52010/041240.

(Continued)

*Primary Examiner* — Nicholas Lucchesi
*Assistant Examiner* — Gerald Landry, II
(74) *Attorney, Agent, or Firm* — Foley & Lardner LLP

(57) ABSTRACT

A reservoir may be filled with fluidic media in a first type of environment, a plunger head may be placed within the reservoir in the first type of environment, and a casing that may be configured to envelop at least a portion of a plunger arm operatively connected to the plunger head may be attached adjacent to at least a portion of the reservoir in a second type of environment. A reservoir may be provided having a first and second portion for respectively containing fluidic media, the second portion may be adapted to be removable, the reservoir may be selectively filled with a first volume or a second volume of fluidic media, a seal member may be placed in the reservoir, and the second portion may be removed in a case where the reservoir contains the first volume of fluidic media.

18 Claims, 14 Drawing Sheets

(56) References Cited

U.S. PATENT DOCUMENTS

| | | |
|---|---|---|
| 2004/0159364 A1 | 8/2004 | Landau et al. |
| 2005/0020980 A1* | 1/2005 | Inoue et al. .................. 604/152 |
| 2006/0264894 A1 | 11/2006 | Moberg et al. |
| 2007/0073235 A1 | 3/2007 | Estes et al. |
| 2007/0169435 A1 | 7/2007 | Kinney et al. |
| 2007/0185450 A1 | 8/2007 | De Polo et al. |
| 2008/0077081 A1* | 3/2008 | Mounce et al. ................ 604/67 |
| 2008/0306436 A1 | 12/2008 | Edwards et al. |
| 2009/0126596 A1 | 5/2009 | Threlkel |

OTHER PUBLICATIONS

Search Report dated Mar. 2, 2011 from related PCT application No. PCT/US2010/041240.

US Office Action dated Mar. 3, 2011 from related patent application No. 12/499,283.

\* cited by examiner

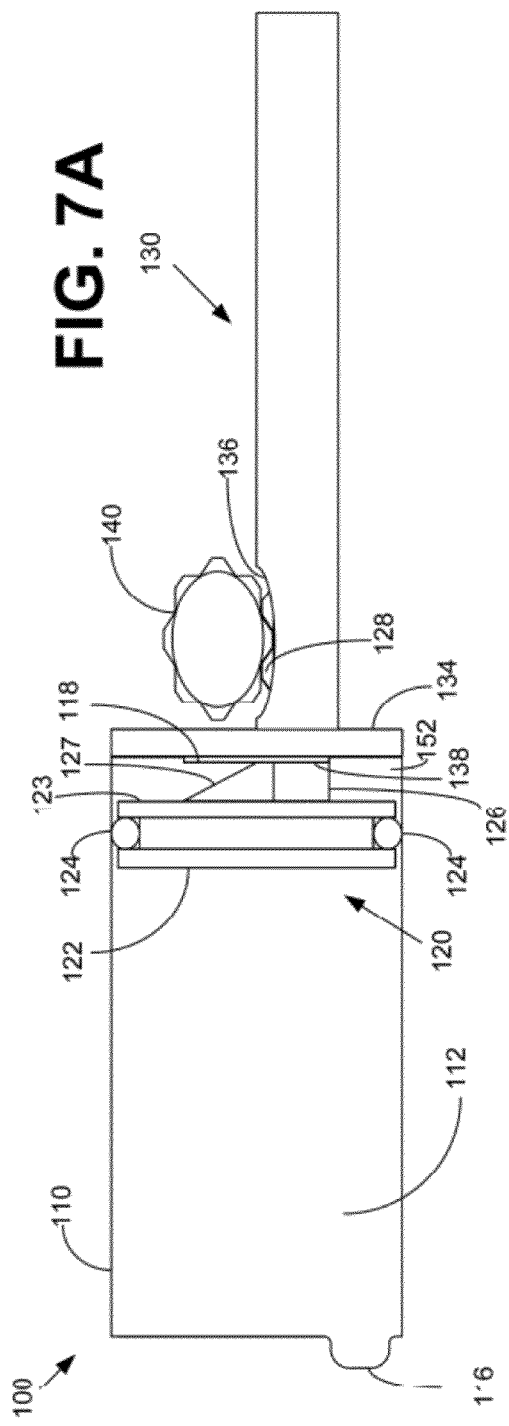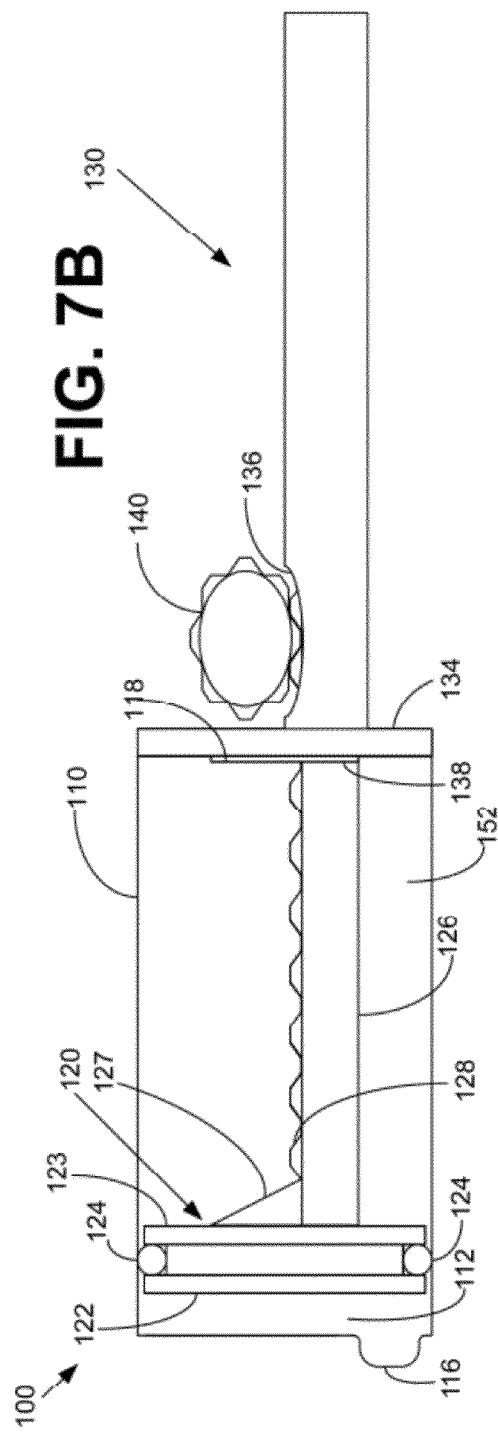

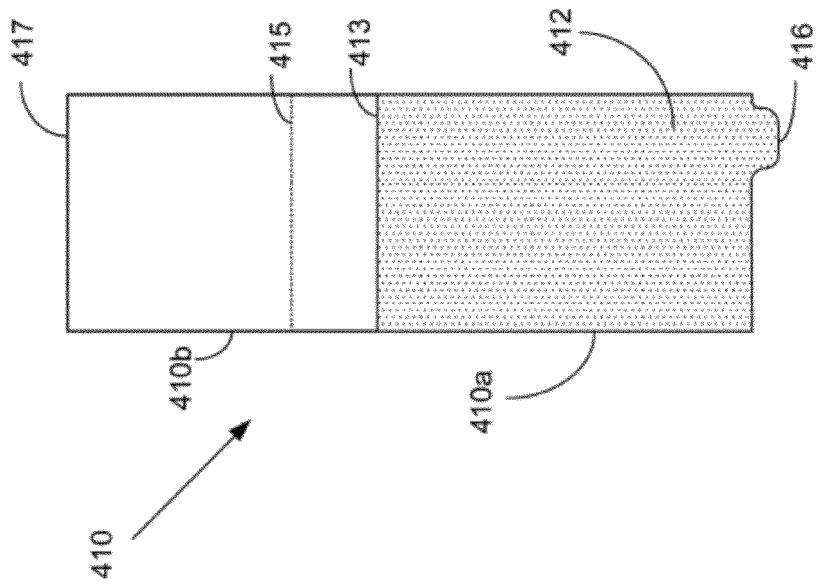
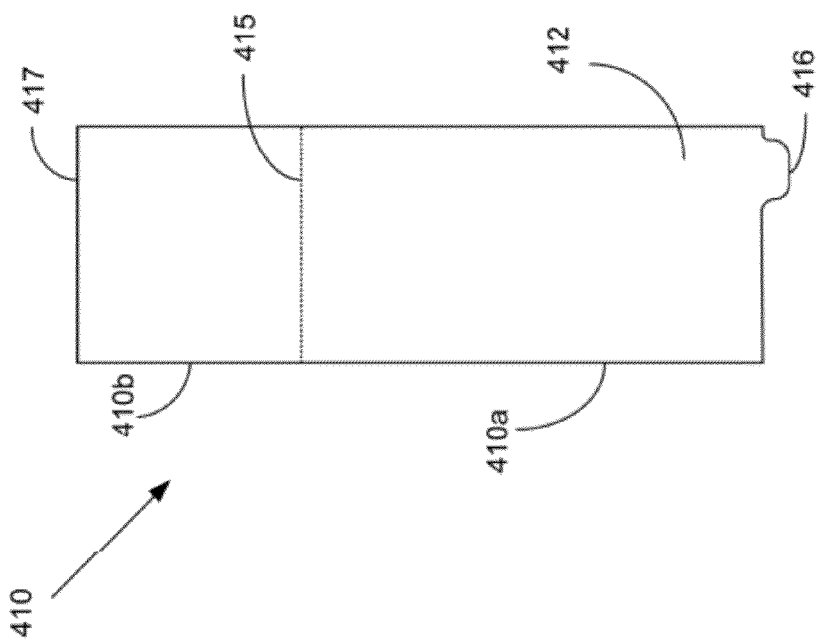

RESERVOIR FILLING SYSTEMS AND METHODS

CROSS-REFERENCE TO RELATED PATENT APPLICATIONS

This application is a Divisional of U.S. application Ser. No. 12/499,283, filed Jul. 8, 2009, incorporated herein by reference in its entirety.

BACKGROUND OF THE INVENTION

1. Field of the Invention

Embodiments of the present invention relate generally to systems and methods that include reservoirs for containing fluidic media and having movable plungers and, in specific embodiments, to infusion medium delivery systems and methods employing such reservoirs.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A method of making a system for transferring fluidic media may include, but is not limited to, any one or combination of: (i) filling an interior volume of a reservoir body with fluidic media in a first type of environment; (ii) placing a plunger head within the reservoir body in the first type of environment, the plunger head may be adapted to be moveable in an axial direction within the reservoir body; and (iii) attaching a casing adjacent to at least a portion of the reservoir body in a second type of environment, the casing may be configured to envelop at least a portion of a plunger arm operatively connected to the plunger head, the casing may be further configured to allow the plunger arm to move in the axial direction relative to the reservoir body and at least partially within the reservoir body.

In various embodiments, the first type of environment may be an aseptic environment. In some embodiments, the aseptic environment may be free of at least one of contaminants and pathogens.

In various embodiments, the second type of environment may not be an aseptic environment. In various embodiments, the method may further include operatively connecting the plunger arm to the plunger head in the second type of environment. In various embodiments, the plunger arm may be operatively connected to the plunger head before the casing is attached to the reservoir body.

In various embodiments, the method may further include locating the plunger arm at least partially in the casing and operatively connecting the plunger arm to the plunger head after the casing is attached to the reservoir body. In various embodiments, the plunger arm and the plunger head may be integral to one another.

In various embodiments, attaching a casing adjacent to at least a portion the reservoir body may comprise welding the casing to the reservoir body. In some embodiments, the casing may be laser welded to the reservoir body.

A method of making a system for containing fluidic media may include, but is not limited to any one or combination of: (i) providing a reservoir body having a first portion and a second portion for respectively containing fluidic media; (ii) adapting the second portion to be removable from the reservoir body; (iii) selectively filling the reservoir body with one of a first volume of fluidic media and a second volume of fluidic media; (iv) placing a seal member in the reservoir body, the seal member to be arranged in at least one of the first portion and the second portion of the reservoir body; and (v) removing the second portion in a case where the first portion is sufficiently filled with the first volume of fluidic media and the seal member is arranged at least partially in the first portion of the reservoir body.

In various embodiments, adapting the second portion may include scoring a perimeter around the reservoir body. The perimeter may be for separating the first portion of the reservoir body and the second portion of the reservoir body.

In various embodiments, adapting the second portion may include forming a perimeter around the reservoir body. The perimeter may be for separating the first portion of the reservoir body and the second portion of the reservoir body. In some embodiments, a thickness of the reservoir body along the perimeter may be less than a thickness of the first portion of the reservoir body. In some embodiments, a portion of the reservoir body corresponding to the perimeter may be made of a different material than a material of the first portion of the reservoir body. In some embodiments, the perimeter may comprise perforations around the reservoir body.

In various embodiments, a thickness of the first portion of the reservoir body may be less than a thickness of the second portion of the reservoir body. In various embodiments, the second portion of the reservoir body may be made of a material different from a material of the first portion of the reservoir body.

In various embodiments adapting the second portion may include providing an annular body sized and dimension to fit around at least a portion of the reservoir body. The annular body may be for separating the first portion of the reservoir body and the second portion of the reservoir body.

In various embodiments, at least one of selectively filling the reservoir body and placing a seal member in the reservoir body occurs in an aseptic environment. In some embodiments, the second portion may be removed from the reservoir body in an environment that is not aseptic.

In various embodiments, the seal member may comprise a plunger head arranged for movement within the reservoir body. In some embodiments, the method may include operatively connecting a plunger arm to the plunger head. In further embodiments, the plunger arm and the plunger head may be integral to one another.

In some embodiments, the method may include attaching a casing adjacent to at least a portion the reservoir body. The casing may be configured to envelop at least a portion of a plunger arm operatively connected to the plunger head. The casing may be further configured to allow the plunger arm to move in an axial direction relative to the reservoir body and at least partially within the reservoir body.

In further embodiments, the method may include locating the plunger arm at least partially in the casing and operatively connecting the plunger arm to the plunger head after the casing is attached to the reservoir body. In further embodiments, attaching a casing adjacent to at least a portion the reservoir body may comprise welding the casing to the reservoir body. In yet further embodiments, the casing may be laser welded to the reservoir body.

In various embodiments, selectively filling the reservoir body may include filling the reservoir body to a fill line. In some embodiments, a volume of fluidic media for filling the reservoir body to the fill line may correspond to one of the first volume of fluidic media and the second volume of fluidic media. In some embodiments, the seal member may be located in the reservoir body to contact fluidic media at the fill line.

In various embodiments, the seal member may be placed in the first portion of the reservoir body in a case where the reservoir body contains a volume equal to the first volume of fluidic media. The seal member may be located in the second portion of the reservoir body in a case where the reservoir body contains a volume equal to the second volume of fluidic media.

A system for containing fluidic media may include, but is not limited to, a reservoir body and a plunger head. The reservoir body may have an interior volume for containing one of a first amount of fluidic media and a second amount of fluidic media. The reservoir body may include a first portion and a second portion.

The first portion may have an interior volume corresponding to a first part of the interior volume of the reservoir body. The interior volume of the first portion may be for containing a volume equal to the first amount of fluidic media. The second portion may have an interior volume corresponding to a second part of the interior volume of the reservoir body. The interior volume of the first portion and the interior volume of the second portion may be for collectively containing a volume equal to the second amount of fluidic media.

The plunger head may be located in at least one of the first portion and the second portion of the reservoir body. The second portion may be adapted to be removable from the first portion. The second portion may be removed in a case where the plunger head is at least partially in the first portion and the interior volume of the reservoir body contains a volume of fluidic media equal to the first amount of fluidic media.

In various embodiments, the reservoir body may have a perimeter around the reservoir body. The perimeter may separate the first portion of the reservoir body and the second portion of the reservoir body.

BRIEF DESCRIPTION OF THE DRAWINGS

FIGS. 7A and 7B illustrate a cross-section of a system for transferring fluidic media in accordance with an embodiment of the present invention;

FIG. 14A illustrates a cross-section of a reservoir body in accordance with an embodiment of the present invention;

FIG. 14B illustrates a cross-section of a reservoir body in accordance with an embodiment of the present invention;

DETAILED DESCRIPTION OF THE PREFERRED EMBODIMENTS

Figure 1:
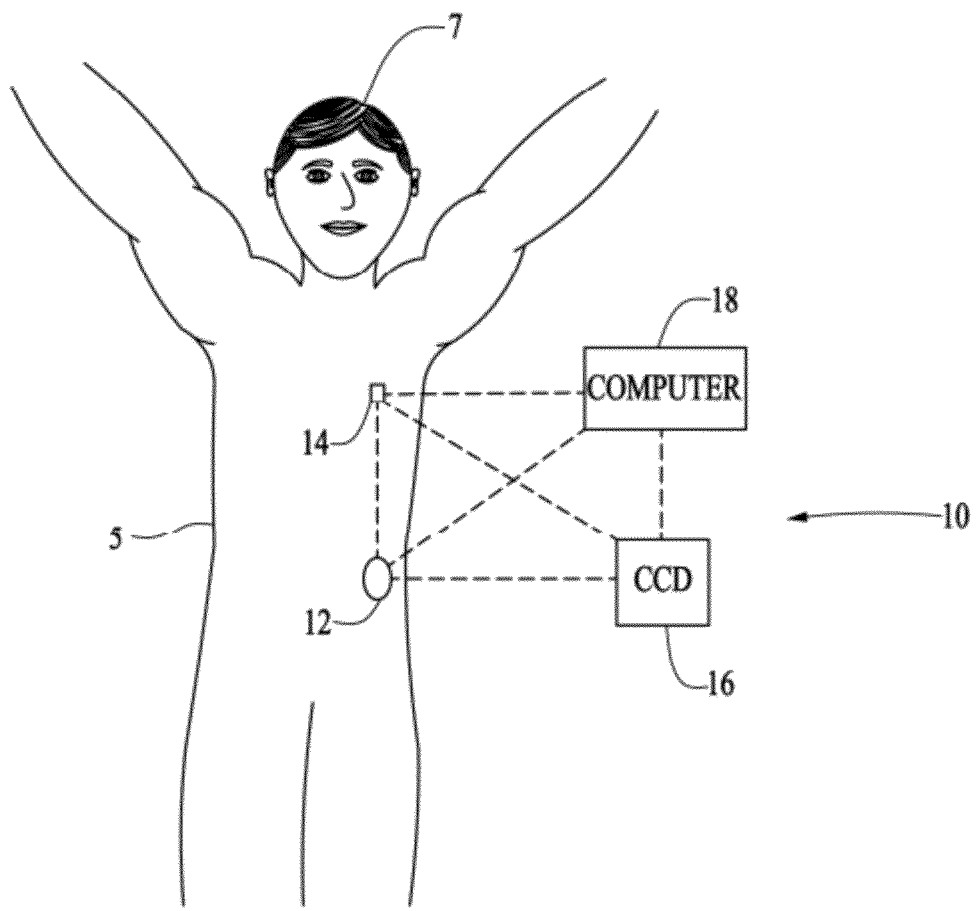
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples. It should be noted user-patient as used throughout the disclosure or similar term may include patient-user, patient, or user (e.g., a patient, a medical professional, or other treating the patient).

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604, 172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645, 993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir". In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
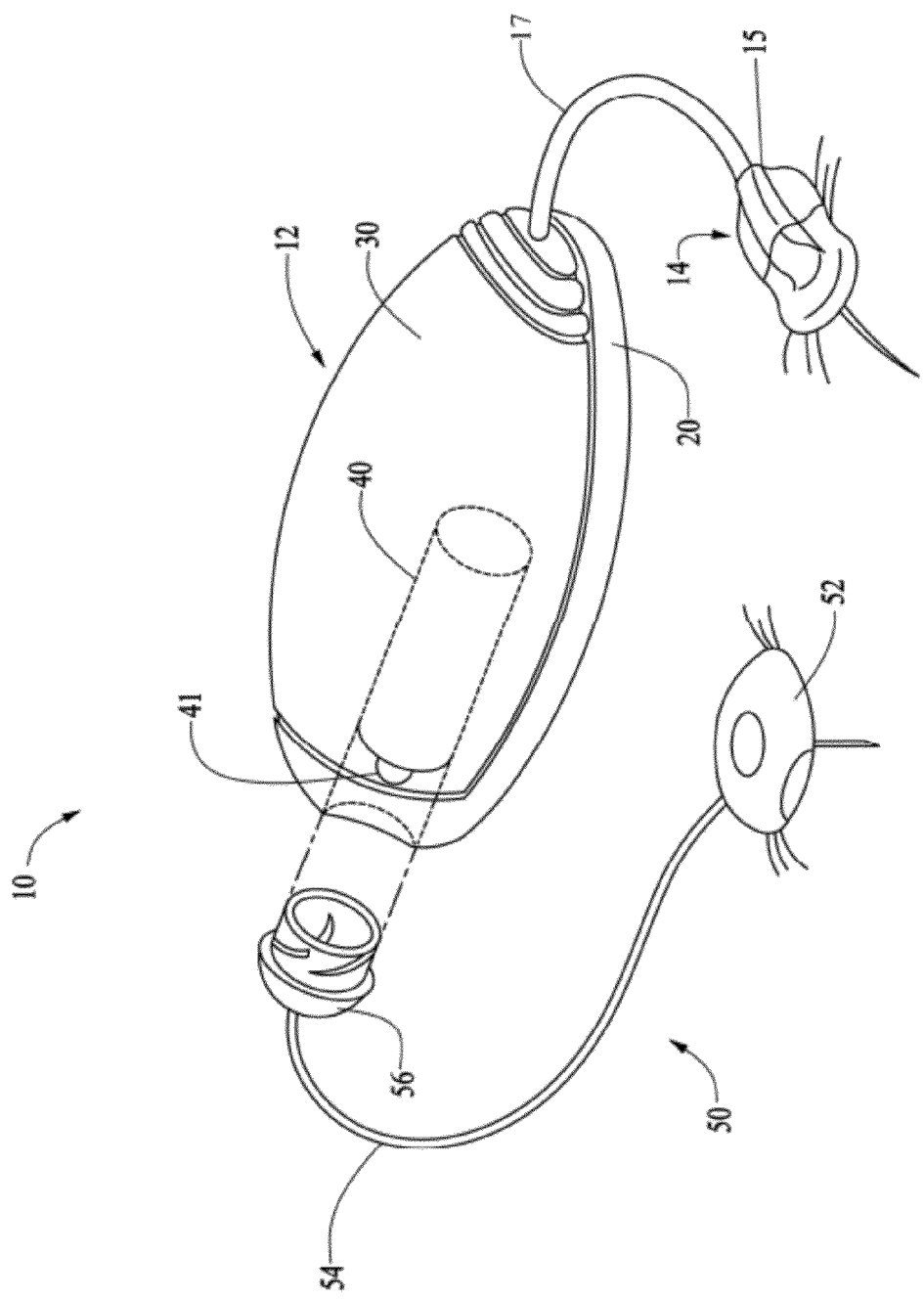
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
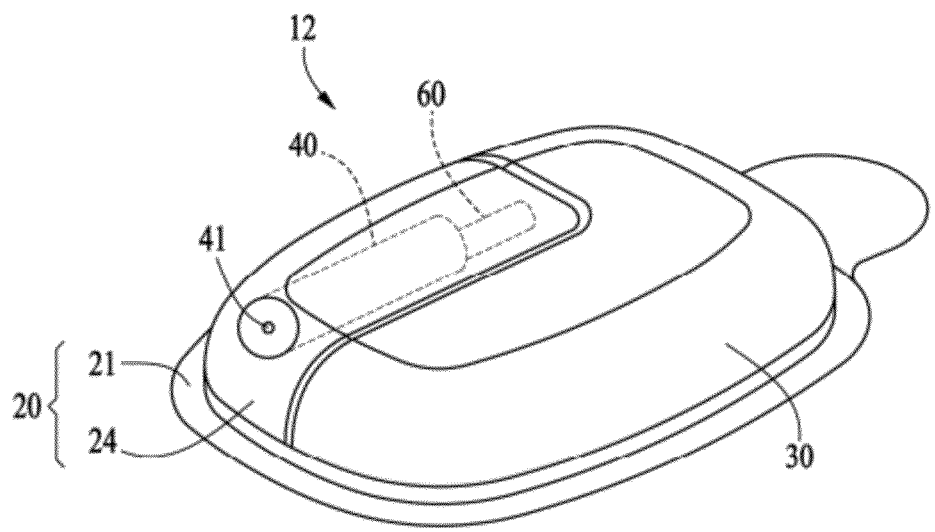
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2.

While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
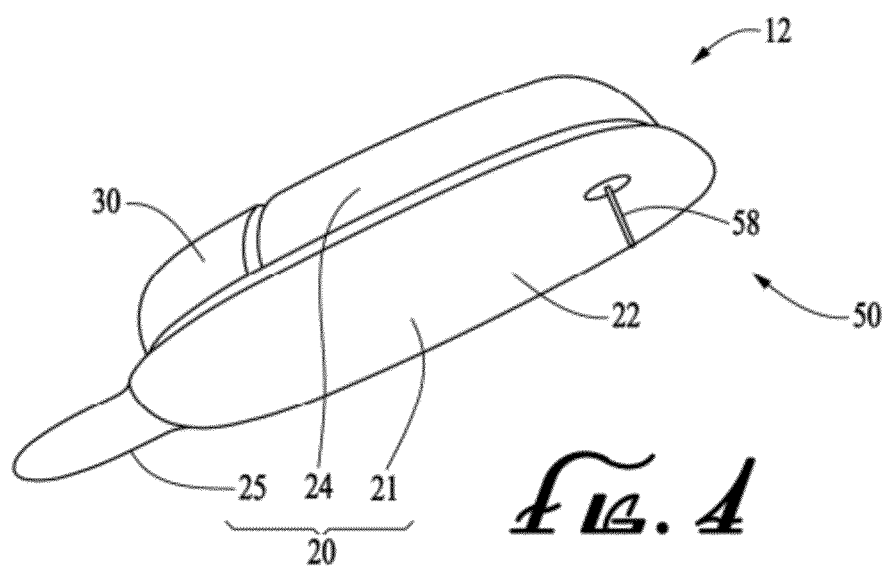
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
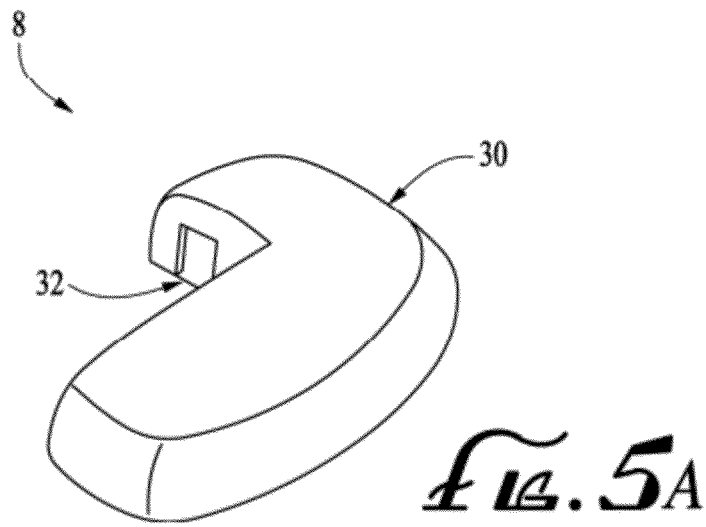
FIG. 5A illustrates a durable portion of a delivery device in accordance with an embodiment of the present invention.
Figure 5B:
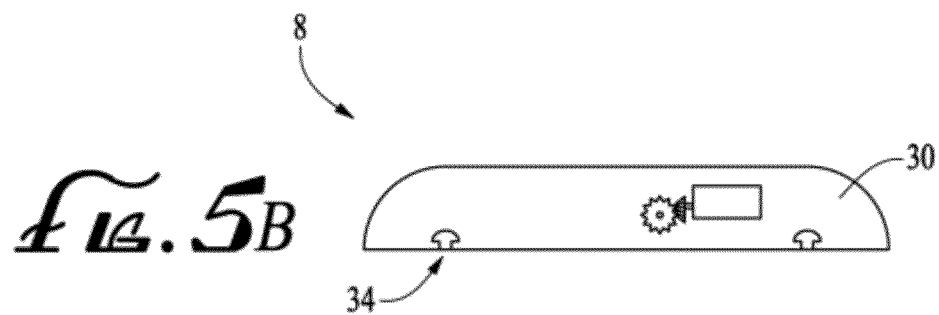
FIG. 5B illustrates a section view of a durable portion of a delivery device in accordance with an embodiment of the present invention.
Figure 5C:
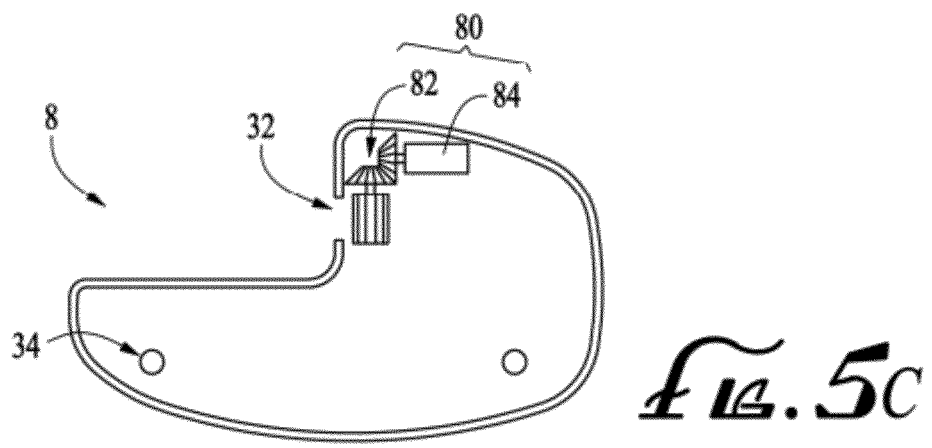
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
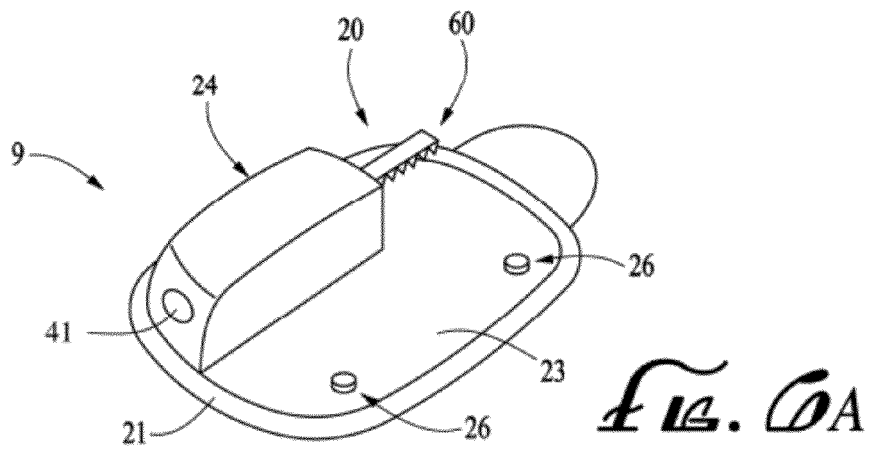
FIG. 6A illustrates a disposable portion of a delivery device in accordance with an embodiment of the present invention.
Figure 6B:
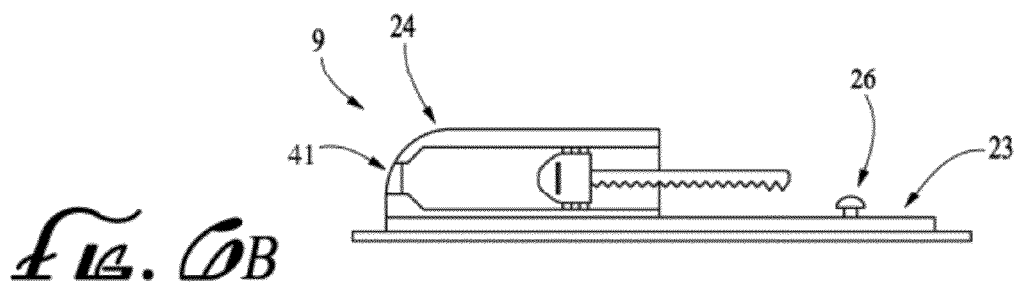
FIG. 6B illustrates a section view of a disposable portion of a delivery device in accordance with an embodiment of the present invention.
Figure 6C:
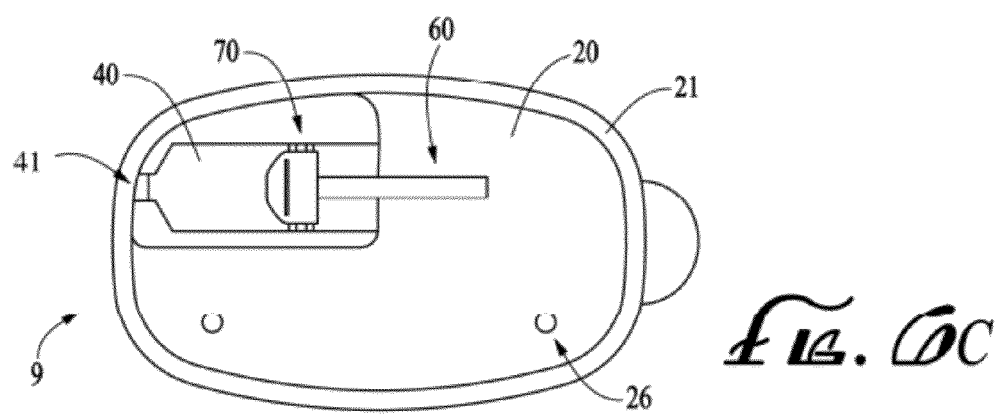
FIG. 6C illustrates a section view of a disposable portion of a delivery device in accordance with an embodiment of the present invention.
Figure 8:
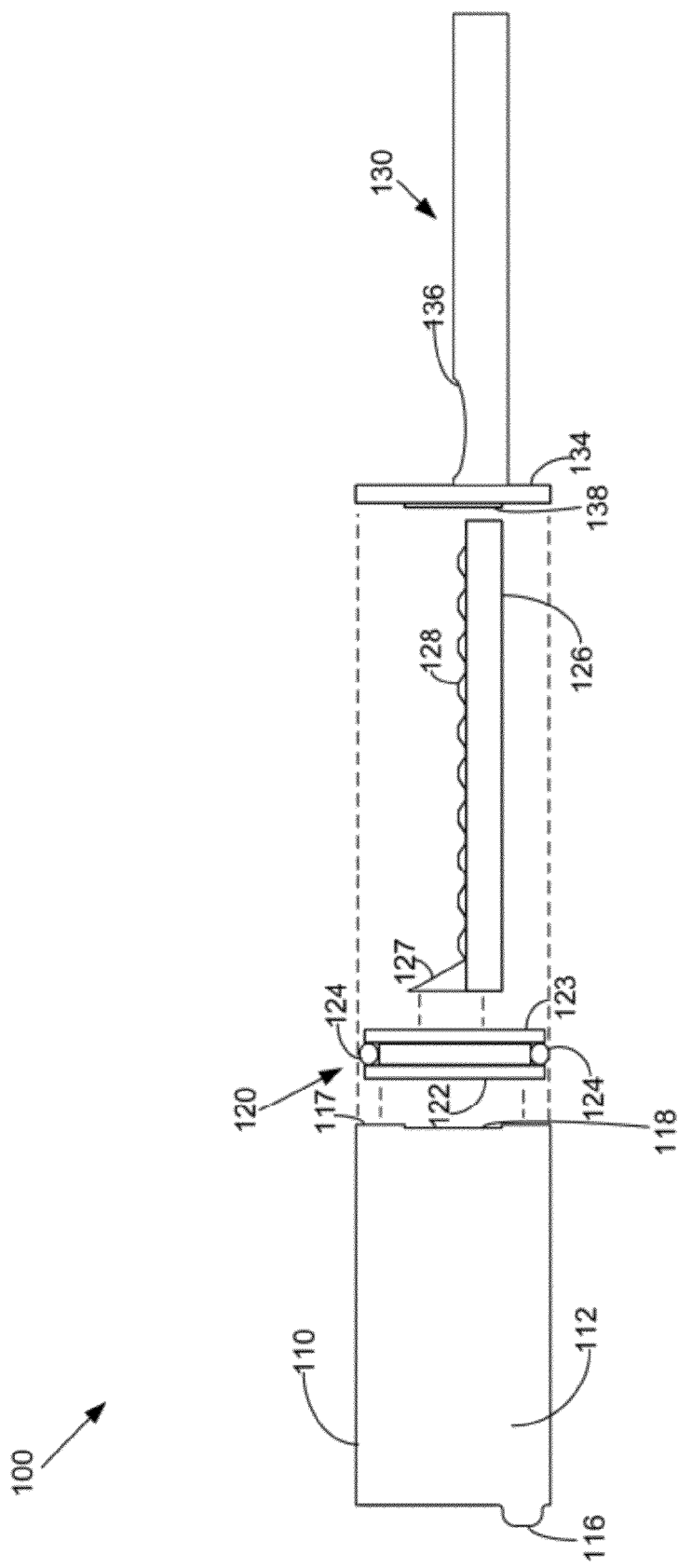
FIG. 8 illustrates an exploded view of a system for transferring fluidic media in accordance with an embodiment of the present invention.
Figure 9:
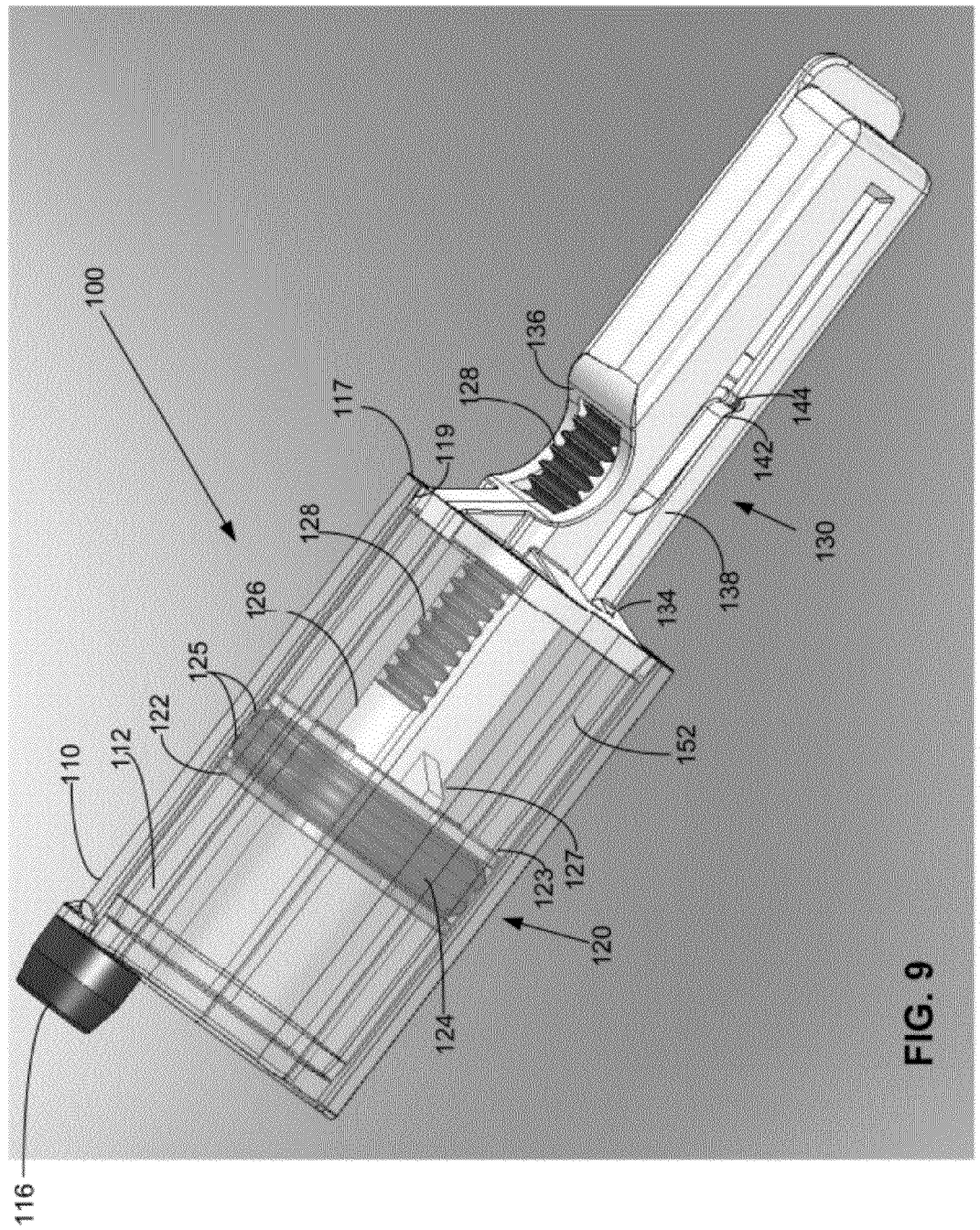
FIG. 9 illustrates a system for transferring fluidic media in accordance with an embodiment of the present invention.
Figure 10:
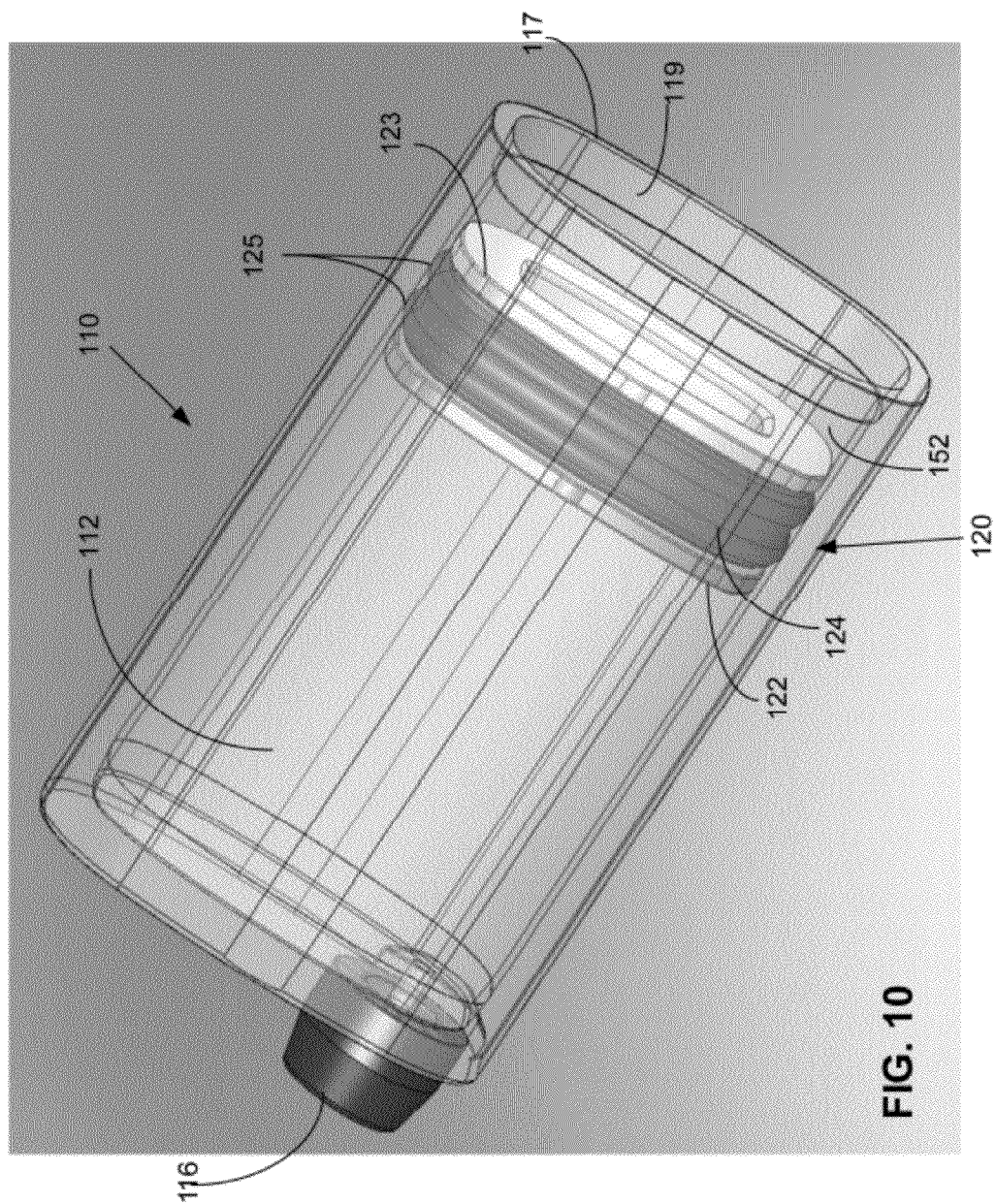
FIG. 10 illustrates a portion of a system for transferring fluidic media in accordance with an embodiment of the present invention.
Figure 11:
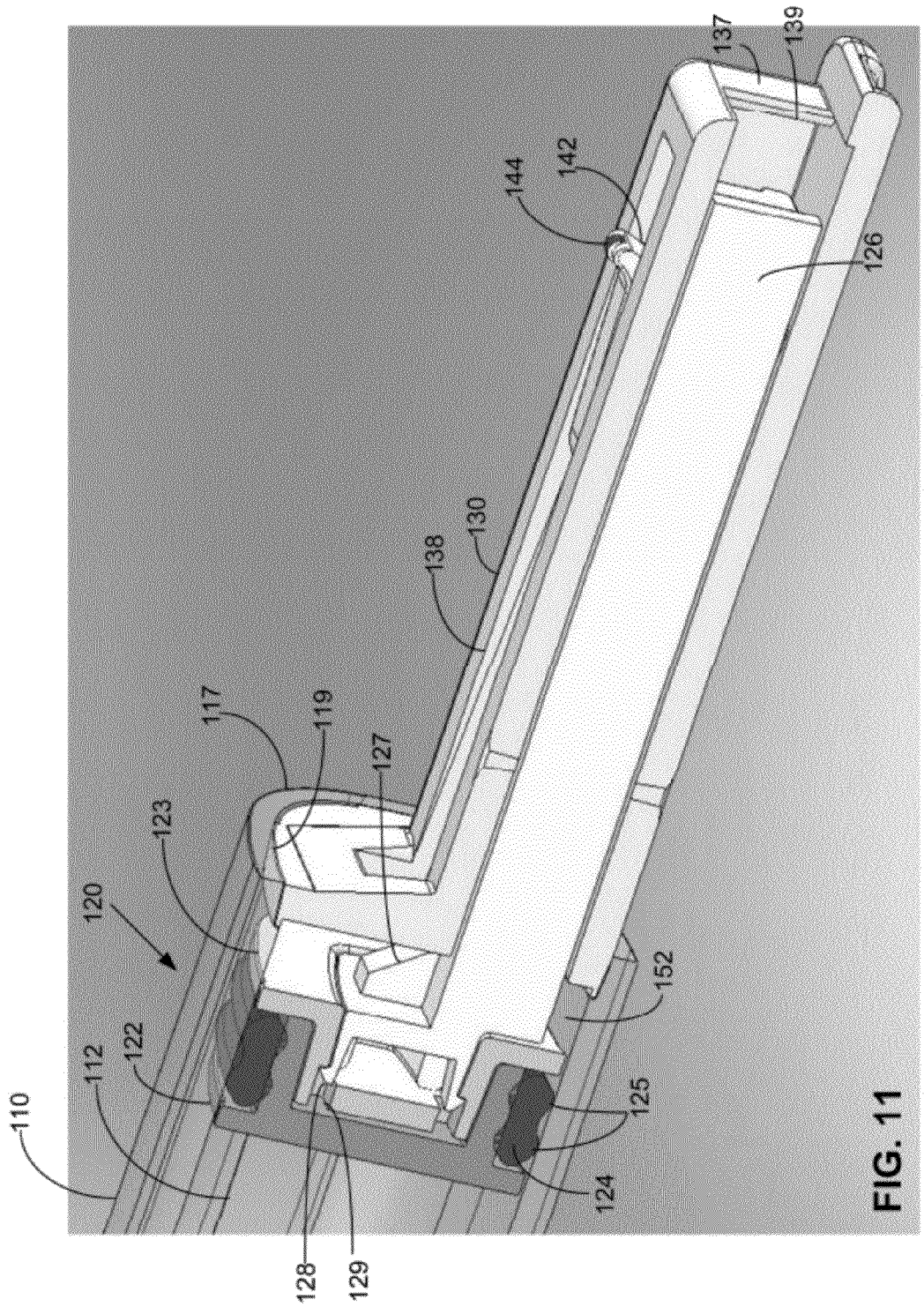
FIG. 11 illustrates a cross-section of a portion of a system for transferring fluidic media in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown) related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

FIGS. 7A-11 illustrate a reservoir system 100. The reservoir system 100 and/or a process 200 (discussed later) for filling the reservoir system 100 (e.g., reservoir body 110) may be similar to or employed as an embodiment of the reservoir system 40 (e.g., FIGS. 1-6C). Although the reservoir system 100 and/or a process 200 (discussed later) for filling the reservoir system 100 may include features similar or used with the embodiments of FIGS. 1-6C, it should be understood that the reservoir system 100 and/or the process 200 for filling the reservoir system 100 may also include some or all of the same features and operate in a manner similar to that shown and described in the embodiments of FIGS. 13-14D. In addition, some or all of the features shown in FIGS. 1-6C and 13-14D may be combined in various ways and included in the embodiments shown in FIGS. 7A-12. Likewise, it should be understood that any of the features of the embodiments of FIGS. 7A-12 may be combined or otherwise incorporated into any of the other embodiments of FIGS. 7A-12 as well as any other embodiment herein discussed.

The reservoir system 100 may include, but is not limited to, a container or reservoir body 110, a plunger head 120, a plunger arm 126, and a plunger arm casing 130. The reservoir body 110 may have an interior volume 112 for containing fluidic media. In various embodiments, the reservoir body 110 may be made of various suitable materials, including, but not limited to, glass, plastic, TOPAS® polymers (or any other cyclic olefin copolymer (or polymer)), or the like. The reservoir body 110 may be of any suitable shape and/or size and may be adapted to hold any volume of fluidic media depending on needs of user-patients.

The reservoir body 110 may have a port 116 for expelling fluidic media contained in the interior volume 112 of the reservoir body 110. In various embodiments, the port 116 of the reservoir body 110 may be for allowing fluidic media to flow into the interior volume 112 of the reservoir body 110 (i.e., to fill the interior volume 112 of the reservoir body 110). In other embodiments, the interior volume 112 of the reservoir body 110 may be filled with fluidic media through an end 117, which may be open. For example, the end 117 may be on an opposite side of the reservoir body 110 from the port 116. In other embodiments, the interior volume 112 of the reservoir body 110 may be filled with fluidic media through a second port (not shown), which may be, for example, on a same side of the reservoir body 410 as the port 116.

The plunger head 120 may be located within the reservoir body 110 and may be moveable in an axial direction of the reservoir body 110 to expand (e.g., FIG. 7A) or contract (e.g., FIG. 7B) the interior volume 112 of the reservoir body 110. The plunger head 120 may be advanced within the reservoir body 110 to expel fluidic media contained in the interior volume 112 of the reservoir body 110 out the port 116 of the reservoir body 110. The plunger head 120 or a portion thereof may be made of Bromobutyl rubber, silicone rubber, or any other suitable material and/or any derivative thereof. The plunger head 120 may have a front portion 122 and a rear portion 123.

The front portion 122 of the plunger head 120 may be in contact with fluidic media contained in the interior volume 112 of the reservoir body 110. In some embodiments, the front portion 122 of the plunger head 120 may comprise a material compatible with fluidic media contained in the interior volume 112 of the reservoir body 110. In such embodiments, any number of the remaining portions of the plunger head 120, such as the rear portion 123 of the plunger head 120, the plunger arm 126, and the plunger arm casing 130 may be made of a similar material or of any suitable material, including, but not limited to, materials incompatible with fluidic media contained in the interior volume 112 of the reservoir body 110.

In some embodiments, where the interior volume 112 of the reservoir body 110 is for containing insulin, the front portion 122 of the plunger head 120 may comprise an insulin compatible material, such as, but not limited to, polyethylene, or the like. In such embodiments, any number of the remaining portions of the plunger head 120, such as the rear portion 123 of the plunger head 120, the plunger arm 126, and the plunger arm casing 130 may be made of an insulin compatible material, which may be the same or different from that of the front portion 122, or of any suitable material, including, but not limited to, materials incompatible with insulin.

In some embodiments, the front portion 122 of the plunger head 120 may be removably attachable to the plunger head 120. For example, the front portion 122 of the plunger head 120 may have one or more tabs (not shown) configured to fit into one or more apertures (not shown) located on the plunger head 120. In various embodiments, the front portion 122 of the plunger head 120 may be secured to the plunger head 120 in any suitable manner, such as, but not limited to, a snap-fitting, an adhesive, friction fitting, laser welding, magnetic coupling, or the like.

The rear portion 123 of the plunger head 120 may be connected or connectable to an end of the plunger arm 126 in any suitable manner. For example, the rear portion 123 of the plunger head 120 may include an aperture 129 for receiving a tab 128 or the like of the plunger arm 126. The tab 128 may be snap-fit into the aperture 129 to connect the plunger arm 126 to the rear portion 123 of the plunger head 120. In various other embodiments, the plunger arm 126 may be connected to the plunger head 120 and/or the rear portion 123 of the plunger head 120 in any suitable manner, such as, but not limited to, an adhesive, friction fitting, laser welding, magnetic coupling, or the like.

The plunger arm 126 may be moveable in an axial direction within the plunger arm casing 130 and the reservoir body 110. In some embodiments, the plunger arm 126 and the rear portion 123 of the plunger head 120 may be integral to one another. In other embodiments, the plunger arm 126 and the rear portion 123 of the plunger head 120 may be separate components.

The plunger arm 126 may include an engagement side 128 for operatively engaging a drive member 140, drive linkage, or the like. For example, the engagement side 128 of the plunger arm 126 and the drive member 140 may be complementing gears, complementing threaded members, or the like, that may operatively engage one another. The drive member 140 may be a drive screw, drive rack, or the like. The drive member 140 may be connected to a motor (not shown) to move the drive member 140 to cause the plunger arm 126 to move within the plunger arm casing 130 and the reservoir body 110 and, thus move the plunger arm 120 within the reservoir body 110 to expand or contact the interior volume 112 of the reservoir body 110.

The plunger arm casing 130 may be for supporting the plunger arm 126 as the plunger arm 126 moves along the plunger arm casing 130, for example, by the drive member 140. At least one side of the plunger arm 126 may be in contact with one or more interior sides of the plunger arm casing 130. In some embodiments, the plunger arm casing 130 may be for aligning the plunger arm 126 as the plunger arm 126 moves along the reservoir body 110, for example, by the drive member 140. In addition, the plunger arm casing 130 may be sized and configured to substantially envelop the plunger arm 126, for example, in a case where the plunger head 120 is drawn substantially near the end 117 of the reservoir body 110 (e.g., FIG. 7A). Thus in some embodiments, the plunger arm 126 may be located within the reservoir body 110 and/or the plunger arm casing 130 during use of the reservoir system 100 by a user-patient (e.g., during delivery of fluidic media to the user-patient).

In some embodiments, the plunger arm casing 130 may have an opening 136 for allowing a portion of the engagement side 128 of the plunger arm 126 to operatively engage the drive member 140. In such embodiments, the plunger arm 126 may be surrounded by the plunger arm casing 130 and/or the reservoir body 110. Accordingly in such embodiments, only the portion of the engagement side 128 of the plunger arm 126 exposed by the opening 136 may be free from (i.e., not surrounded by) the plunger arm casing 130 and/or the reservoir body 110. This may allow the drive member 140 to operatively engage the engagement side 128 of the plunger arm 126 while the plunger arm 126 or a portion thereof remains in the plunger arm casing 130 and/or the reservoir body 110.

The reservoir system 100 may include a reservoir cover (or casing) 134 that may be sized and configured to cover the end 117 of the reservoir body 110. For example, in a case where the port 116 is located on a first end of the reservoir body 110, a second end opposite the first end may be the end 117 of the reservoir body 110 and may be covered by the reservoir cover 134. The reservoir cover 134 may be integral with the plunger arm casing 130.

In other embodiments, the reservoir cover 134 may be separate from the plunger arm casing 130. For example, the reservoir cover 134 may be removably attachable to the plunger arm casing 130. In such embodiments, the reservoir cover 134 may be connected to or connectable to the plunger arm casing 130 in any suitable manner, such as those previously described.

In some embodiments, the end 117 of the reservoir body 110 may be open. The reservoir cover 134 may cover the open end 117 of the reservoir body 110 or be configured to fit within or to the open end 117 of the reservoir body 110 to seal or close the open end 117 of the reservoir body 110. The open end 117 may allow fluidic media to flow into the interior volume 112 of the reservoir body 110 and/or the plunger head 120 and/or at least a portion of the plunger arm 126 attached to the plunger head 120 to be insertable into the reservoir body 110, for example, before the reservoir cover 134 is placed in/on the reservoir body 110 to cover the open end 117 of the reservoir body 110.

For example, the reservoir cover 134 may include one or more tabs 138 sized and configured to fit within one or more recesses 118 on the end 117 of the reservoir body 110 to attach or otherwise fit the reservoir cover 134 to the reservoir body 110 to substantially close the reservoir body 110 after the plunger head 120 and/or at least a portion of the plunger arm 126 have been placed in the reservoir body 110. However, the reservoir cover 134 may be connected to or connectable to the reservoir body 110 in any suitable manner, such as those previously described.

In some embodiments, the reservoir cover 134 and/or the plunger arm casing 130 may be configured for minimizing an expansion of the reservoir body 110 in one or more dimensions. In such embodiments, by fitting the reservoir cover 134 to the back of the reservoir body 110, the reservoir cover 134 may help retain a shape of the reservoir body 110.

A seal member 124, such as an o-ring or the like, may be positioned between the reservoir body 110 and a portion of the plunger head 120. A portion 125 of the seal member 124 may be in contact with the reservoir body 110. The interior volume 112 of the reservoir body 110 may be on one side of the seal member 124. The reservoir body 110 may have a chamber 152 located on an opposite side of the seal member 124 from the interior volume 112 of the reservoir body 110.

The seal member 124 may be for substantially preventing fluidic media from flowing from the interior volume 112 of the reservoir body 110 to the chamber 152 of the reservoir body 110. The chamber 152 of the reservoir body 110 may be located between the seal member 124 and the reservoir cover 134 in a case where the plunger head 120 is in the reservoir body 110 and the reservoir cover 134 and/or the plunger arm casing 130 are fitted or otherwise attached to the reservoir body 110. In some embodiments, the seal member 124 may be located between the front portion 122 and the rear portion 123 of the plunger head 120.

In some embodiments, the reservoir system 100 may include at least one support flange 127 positioned on the plunger arm 126 and the rear portion 123 of the plunger head 120. The support flange 127 may provide additional structural strength to the plunger arm 126 and/or the plunger head 120. For example, the support flange 127 may have a triangular configuration and be positioned with one side of the support flange 127 connected to a surface of the plunger arm 126 and a second side of the support flange 127 connected to the rear portion 123 of the plunger head 120. In addition to or alternative to, a second support flange (not shown) may be positioned with one side of the second support flange (not shown) connected to a different surface of the plunger arm 126 and a second side of the second support flange (not shown) connected to the rear portion 123 of the plunger head 120.

Figure 12:
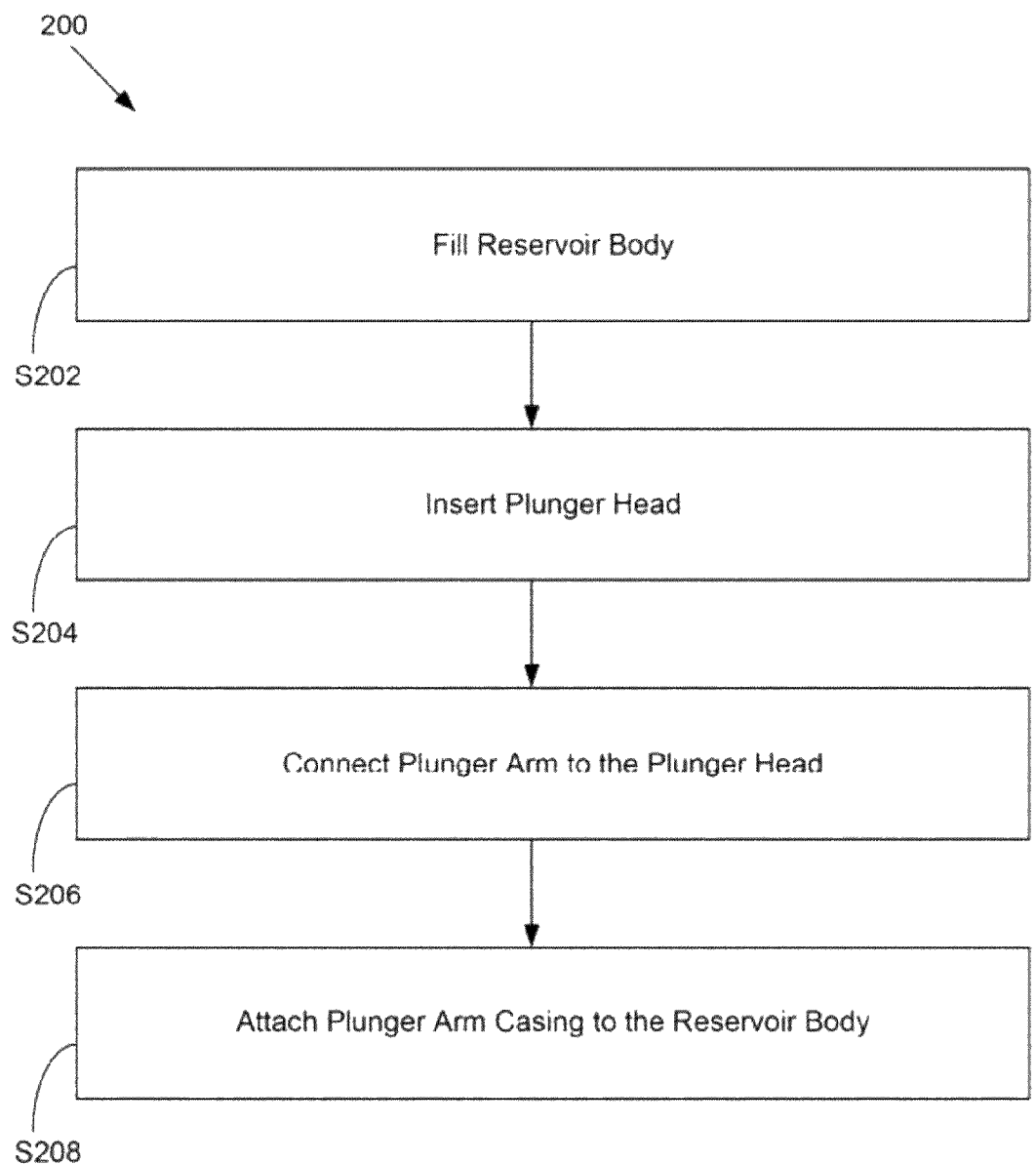
FIG. 12 illustrates a flow chart of a process of making a system for transferring fluidic media in accordance with an embodiment of the present invention.

FIG. 12 illustrates a flowchart for a process 200 for filling a reservoir, such as the reservoir body 110 of FIGS. 7A-11. With reference to FIGS. 7A-12, in step S202, an interior volume 112 of a reservoir body 110 may be filled with fluidic media through an open end 117 of the reservoir body 110. The interior volume 112 of the reservoir body 110 may be filled with fluidic media, for example, in an "aseptic environment." The reservoir body 110 may be filled in any suitable manner such as, but not limited to, pressure filling, vacuum filling, gravity filling (e.g., pouring), and/or the like. The aseptic environment as applied in the pharmaceutical/medical industry may refer to an environment in which assembly of sterilized components and product may be processed in a specialized clean environment. For example, the aseptic environment may be one in which living pathogenic organisms are absent and/or is free of contaminants.

Next in step S204, after the interior volume 112 of the reservoir body 110 is filled with a desired amount, a plunger head 120 may be inserted into the reservoir body 110 through the open end 117 of the reservoir body 110. The plunger head 120 may be positioned to contact the fluidic media contained in the interior volume 112 of the reservoir body 110. The plunger head 120 may serve to seal or otherwise substantially prevent fluidic media from flowing past the plunger head 120, for example, out the reservoir body 110. The plunger head 120 may be inserted into the reservoir body 110 through the open end 117 of the reservoir body 110, for example, in an aseptic environment as was described previously. In some embodiments, this aseptic environment may be a different aseptic environment than the aseptic environment where the reservoir body 110 is filled with fluidic media.

Next in step S206, after the plunger head 120 is inserted into the reservoir body 110, a plunger arm 126 may be connected to the plunger head 120. For instance, as previously described, a rear portion 123 of the plunger head 120 may be connected or connectable to an end of the plunger arm 126 in any suitable manner. For example, the rear portion 123 of the plunger head 120 may include an aperture 129 for receiving a tab 128 or the like of the plunger arm 126. The tab 128 may snap-fit to the aperture 129 to connect the plunger arm 126 to the rear portion 123 of the plunger head 120. In various other embodiments, the plunger arm 126 may be connected to the plunger head 120 and/or the rear portion 123 of the plunger head 120 in any suitable manner, such as, but not limited to, an adhesive, friction fitting, laser welding, magnetic coupling, or the like.

In some embodiments, the plunger arm 126 may be connected to the plunger head 120 in a non-aseptic environment, such as a "clean environment," or the like. The clean environment may be a conventional human scale classified clean room or an environment engineered to further reduce the likelihood of contamination by reducing (or as much as is possible eliminating) direct human contact with the product and components being assembled "aseptically." Generally, a clear environment is relatively free of pathogens and/or contaminants, but to a lesser degree than an aseptic environment.

For example, the reservoir body 110 containing fluidic media and the plunger head 120 may be removed from the aseptic environment(s) in which the reservoir body 110 is filled with fluidic media and receives the plunger head 120, and then placed in a clean environment (e.g., one that is relatively free of contaminants, but not as much as the aseptic environment) at which point the plunger arm 126 may be connected to the plunger head 120. In other words, in such embodiments, the plunger arm 126 may be connected to the plunger head 120 in a different environment from the environment(s) of steps S202 and S204. In other embodiments, the plunger arm 126 may be connected to the plunger head 120 in any suitable environment, including (but not limited to) an aseptic environment.

In other embodiments, the plunger arm 126 may be attached or integrated with the plunger head 120 before the plunger head 120 is placed in the reservoir body 110. Thus, by inserting the plunger head 120 into the reservoir body 110, at least a portion of the plunger arm 126 is also placed within the reservoir body 110. In other words, a plunger head may be placed in a reservoir body as part of step S204 along with an attached or integrated plunger arm or a portion thereof, for example, in an aseptic environment.

In step S208, a plunger arm casing 130 for supporting at least a portion of the plunger arm 126 may be attached to the reservoir body 110. The plunger arm casing 130 may include a portion, such as a reservoir cover (or casing) 134 that may be sized and configured to cover the open end 117 of the reservoir body 110 and/or otherwise attach to the reservoir body 110. As such, the reservoir cover 134 may cover the open end 117 of the reservoir body 110 or be configured to fit within or onto the open end 117 of the reservoir body 110 to seal or close the open end 117 of the reservoir body 110. For example, the reservoir cover 134 may be configured to be friction-fit with an inner rear portion 119 of the reservoir body 110. As such, the plunger arm casing 130 may cover the open end 117 and be attached to the reservoir body 110. Or for example, the reservoir cover 134 may include one or more tabs 138 sized and configured to fit within one or more recesses 118 on or near the open end 117 of the reservoir body 110 to fit the reservoir cover 134 to the reservoir body 110 to substantially close the reservoir body 110 after the plunger head 120 and/or at least a portion of the plunger arm 126 have been placed in the reservoir body 110.

In some embodiments, the plunger arm casing 130 and/or the reservoir cover 134 may be welded (e.g., laser welded) or the like to the reservoir body 110. Such embodiments, may allow, for example, for substantially preventing substances (e.g., contaminants, fluidic media) from going in to or out of the reservoir body 110.

In some embodiments, the reservoir body 110 containing fluidic media and the plunger head 120 may be removed from the aseptic environment(s) in which the reservoir body 110 is filled with fluidic media and receives the plunger head 120, and then placed in a non-aseptic environment, such as a clean environment at which point the plunger arm casing 130 and the reservoir cover 134 may be connected to the reservoir body 110. In other words, in such embodiments, the plunger arm casing 130 and the reservoir cover 134 may be connected to the reservoir body 110 to cover the open end 117 in a different environment from the environment(s) of steps S202 and S204. In other embodiments, the plunger arm casing 130 may be connected to the reservoir body 110 in any suitable environment, including (but not limited to) an aseptic environment.

In various embodiments, step S208 may be performed before step S206 such that the plunger arm casing 130 may be attached to the reservoir body 110 before the plunger arm 126 is attached to the plunger head 120. For example, the plunger arm 126 may be disposed in the plunger arm casing 130 prior to the plunger arm casing 130 and/or the reservoir cover 134 being attached to the reservoir body 110. Once the plunger arm casing 130 and/or the reservoir cover 134 is attached to the reservoir body 110, the plunger arm 126 may be connected to the plunger head 120. In some embodiments, the plunger arm 126 may be guided along the plunger arm casing 130 to connect the plunger arm 126 to the plunger head 120, for example, through an opening 139 in the plunger arm casing 130. For example, a tool (not shown) may be inserted into the opening 139 to guide or otherwise move the plunger arm 126 along the plunger arm casing 130 to connect to the plunger head 120. The plunger arm 126 and/or the plunger head 120 may be adapted to snap-fit together, as described above, or connect in any suitable manner, such as (but not limited to) those previously discussed.

In various embodiments, after the plunger arm 126 is connected to the plunger head 120 and the plunger arm casing 130 and/or the reservoir cover 134 is connected to the reservoir body 110, other drive components, such as a drive motor (not shown) and/or one or more drive members (not shown) operatively connected to the drive motor (not shown) may be operatively connected to the plunger arm 126 as needed. In other embodiments, the other drive components may be connected to or integrated with the plunger head 120 before the plunger head 120 is inserted in the reservoir body 110. For example, a plunger head placed in a reservoir body may have a portion (e.g., a plunger arm) for engaging a drive motor or other drive components. In such embodiments, the integrated components or portions thereof may be placed in the reservoir body 110 along with the plunger head 120 as part of step S204, for example.

Figure 13:
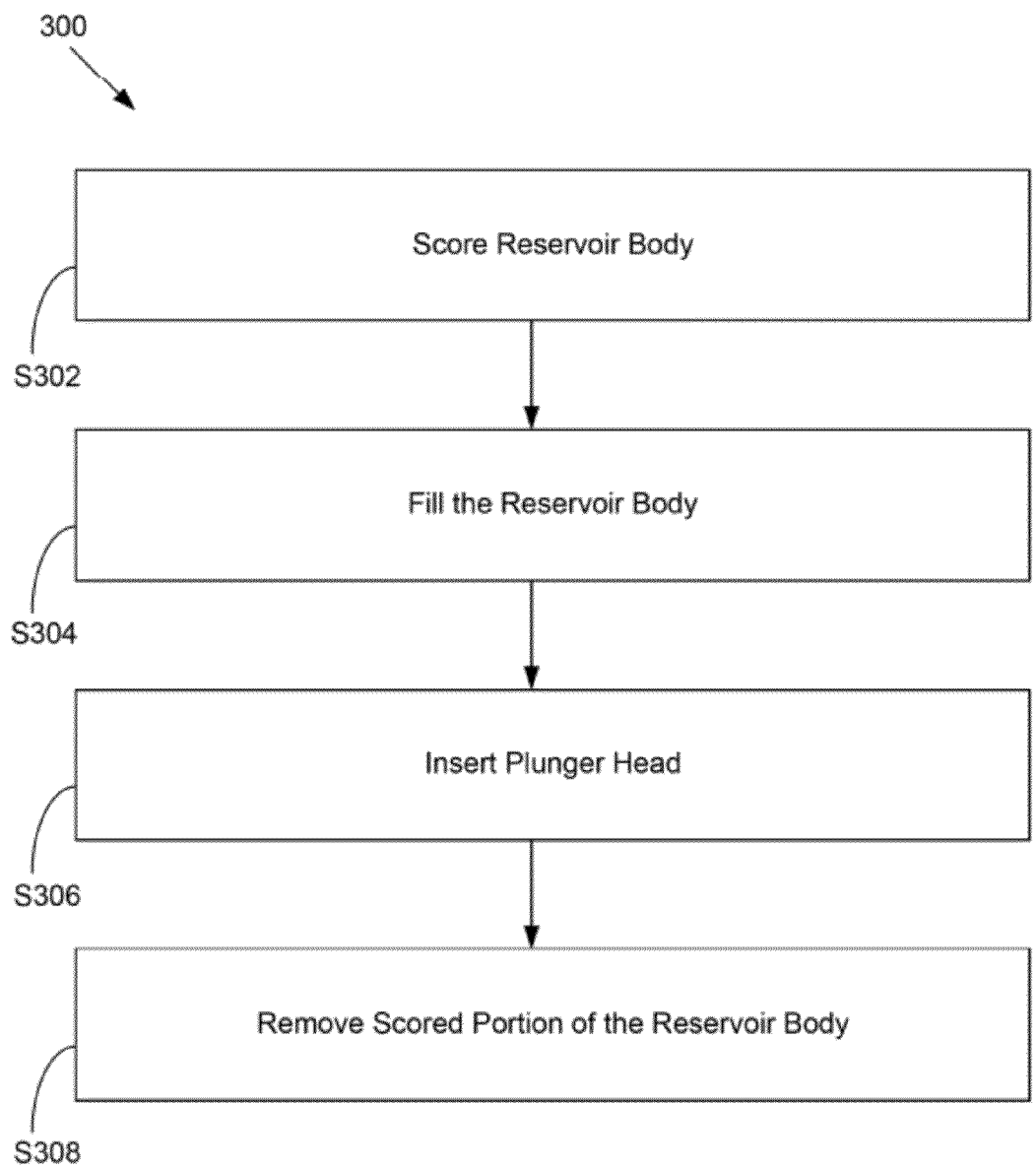
FIG. 13 illustrates a flowchart of a process for making a system for containing fluidic media in accordance with an embodiment of the present invention.

FIG. 13 illustrates a flowchart for a process 300 for filling a reservoir body 410 in accordance with an embodiment of the present invention. In various embodiments, the process 300 may be for filling a reservoir body 410 or the reservoir body 110 of FIGS. 7A-11 (and/or the reservoir system 40 of FIGS. 1-6C). As such, the reservoir body 410 and related components may be like the reservoir body 110 and related components of FIGS. 7A-11 (and/or the reservoir system 40 of FIGS. 1-6C).

The reservoir body 410 and/or the processor 400 for filling the reservoir body 410 may be similar to or employed as an embodiment of the reservoir body 110 and/or the processor 200 (e.g., FIGS. 7A-12). Although the reservoir body 410 and/or the processor 400 for filling the reservoir body 410 may include features similar or used with the embodiments of FIGS. 7A-12, it should be understood that the reservoir body 410 and/or the processor 400 for filling the reservoir body 410 may also include some or all of the same features and operate in a manner similar to that shown and described in the embodiments of FIGS. 1-6C. In addition, some or all of the features shown in FIGS. 1-12 may be combined in various ways and included in the embodiments shown in FIGS. 13-14D. Likewise, it should be understood that any of the features of the embodiments of FIGS. 13-14D may be combined or otherwise incorporated into any of the other embodiments of FIGS. 13-14D as well as any other embodiment herein discussed.

Figure 14D:
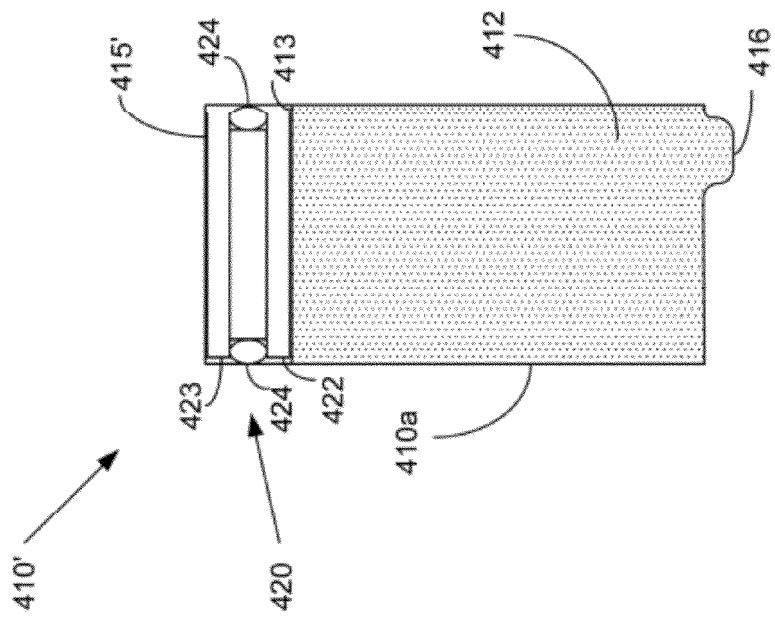
FIG. 14D illustrates a cross-section of a reservoir body in accordance with an embodiment of the present invention.
Figure 14C:
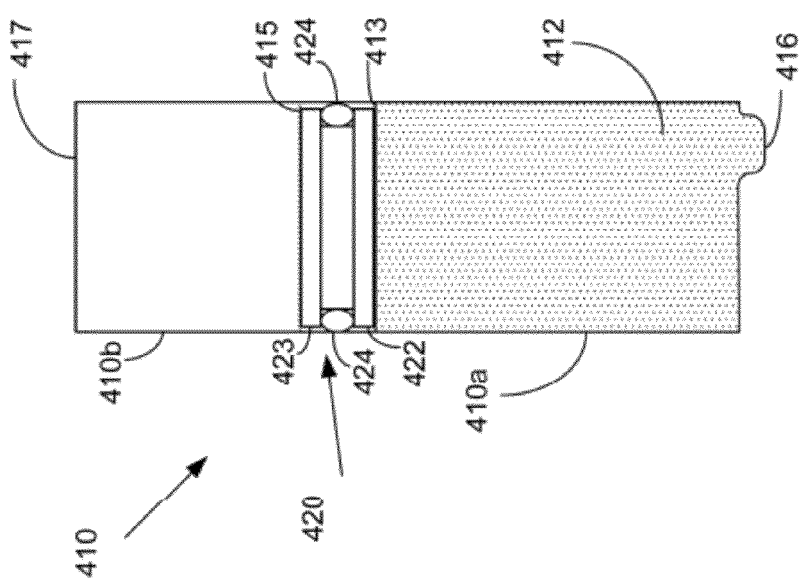
FIG. 14C illustrates a cross-section of a reservoir body in accordance with an embodiment of the present invention.

With reference to FIGS. 13-14D, the reservoir body 410 may have an interior volume 412 for containing fluidic media. In various embodiments, the reservoir body 410 may be made of various suitable materials, including, but not limited to, glass, plastic, TOPAS® polymers (or any other cyclic olefin copolymer (or polymer)), or the like. The reservoir body 410 may be of any suitable shape and/or size and may be adapted to hold any volume of fluidic media depending on needs of user-patients.

The reservoir body 410 may have a port 416 for expelling fluidic media contained in the interior volume 412 of the reservoir body 410. In various embodiments, the port 416 of the reservoir body 410 may be for allowing fluidic media to flow into the interior volume 412 of the reservoir body 410 (i.e., to fill the interior volume 412 of the reservoir body 410). In other embodiments, the interior volume 412 of the reservoir body 410 may be filled with fluidic media through an end 417, which may be open. For example, the end 417 may be on an opposite side of the reservoir body 410 from the port 416. In other embodiments, the interior volume 412 of the reservoir body 410 may be filled with fluidic media through a second port (not shown), which may be, for example, on a same side of the reservoir body 410 as the port 416.

In step S302 (e.g., FIG. 14A), the reservoir body 410 may be scored, pre-cut, perforated, or the like along a perimeter 415 of the reservoir body 410. The reservoir body 410 may be scored during manufacture or after manufacture of the reservoir body 410. The perimeter 415 may bisect (i.e., divide) the reservoir body 410 into a first portion 410a of the reservoir body 410 and a second portion 410b of the reservoir body 410. The perimeter 415 may allow for the removal of the second portion 410b from the reservoir body 410, thus leaving only the first portion 410a of the reservoir body 410. For example, the second portion 410b may be broken off, dissolved, or otherwise removed from the reservoir body 410 to leave the first portion 410a, which may have an end 415' corresponding to where the second portion 410b was removed from the reservoir body 410.

In various embodiments, the perimeter 415 need not extend entirely through the reservoir body 410. In such embodiments, the perimeter 415 need only penetrate the external surface of the reservoir body sufficiently to allow the second portion 410b to be removed from the first portion 410a.

In other embodiments, the perimeter 415 may be formed along the reservoir body 410 during manufacture. For example, the reservoir body 410 may be molded or otherwise formed with a perimeter 415 that allows for removal of the second portion 410b from the reservoir body 410. For instance, a thickness of the reservoir body 110 along the perimeter 415 may be less than a thickness of the first portion 410a and/or a remaining portion of the reservoir body 410. Alternatively, for instance, the perimeter 415 may comprise perforations that allow the second portion 410b to be removed from the first portion 410a.

In other embodiments, the second portion 410b may be formed to allow for removal of the second portion 410b from the reservoir body 410. For example, a thickness of the second portion 410b of the reservoir body 110 may be less than a thickness of the first portion 410a and/or a remaining portion of the reservoir body 410.

In some embodiments, the perimeter 415 (or a portion of the reservoir body 410 corresponding to the perimeter 415) or a portion thereof (e.g., an external surface of the perimeter 415) may be formed of a different material from the first portion 410a and/or the remaining portion of the reservoir body 410. The difference in materials between the perimeter 415 and the first portion 410a and/or a remaining portion of the reservoir body 410 may make it easier to remove (e.g., break off or dissolve) the second portion 410b from the reservoir body 410. For example, the reservoir body 410 or portion thereof may be placed in a substance, such as a liquid or the like, that can dissolve the perimeter 415, but not the reservoir body 410.

In some embodiments, the perimeter 415 may be an annular body (not shown) sized and dimensioned to fit around at least a portion of the reservoir body 410. For example, the annular body (not shown) may fit around or on the reservoir body 410 or in a groove, such as a scored perimeter as discussed, around the reservoir body. In such embodiments, the annular body (not shown) may be, for example, peeled, dissolved, broken off, or otherwise removed to separate the first portion 410a and the second portion 410b or allow for the first portion 410a and the second portion 410b to be separated more easily. For example, the annular body (not shown) may be removed to expose a scored groove or perimeter that seated the annular body (not shown). Then, the second portion 410b may be removed the first portion 410a along the groove.

In other embodiments, the second portion 410b may be made of a different material from the first portion 410a of the reservoir body 410, which may allow the second portion 410 to be removed. For example, the reservoir body 410 or a portion thereof may be placed in a substance, such as a liquid or the like, that can dissolve the second portion 410b, but not the first portion 410a.

In some embodiments, the perimeter 415 may be configured or otherwise formed such that the end 415' may be relatively smooth after the second portion 410b is removed from the reservoir body 410. In some embodiments, the perimeter 415 may be substantially parallel to the end 417 such that the end 415' may be substantially parallel to the end 417 in a case where the second portion 410b is removed. In other embodiments, the perimeter 415 may be scored or otherwise formed in any suitable shape or pattern. For example, the perimeter 415 may be shaped convexly or concavely like a meniscus, or shaped or keyed to receive (e.g., 118 in FIGS. 7A-8) a complementing member (e.g., 138 in FIGS. 7A-8) and/or received by another component after the second portion 410b is removed.

In various embodiments, it should be noted that the perimeter 415 or portions thereof may be in any configuration or arrangement. For example, the perimeter 415 may extend into an external surface of the reservoir body 410 to form a groove around the reservoir body 410. In other examples, the perimeter 415 may extend away from the external surface of the reservoir body 410, such as in a case where the perimeter 415 is an annular member 415 arranged on the reservoir body 410. In yet other examples, the perimeter 415 may be flush with the remainder of the reservoir body 410, such as in a case where the perimeter 415 is made of a material different from the reservoir body 410 and seated in a groove around the reservoir body 410.

In various embodiments, the reservoir body 410 may be manufactured and/or scored in a non-aseptic environment, such as a "clean environment." The clean environment may be a conventional human scale classified clean room or an environment engineered to further reduce the likelihood of contamination by reducing (or as much as is possible eliminating) direct human contact with the product and components being assembled "aseptically" (described later). In other embodiments, the reservoir body 410 may be manufactured and/or scored in any suitable environment, including (but not limited to) an aseptic environment.

Next in step S304 (e.g., FIG. 14B), the interior volume 412 of the reservoir body 410 may be filled with a desired volume of fluidic media. The reservoir body 410 may be filled in any suitable manner such as, but not limited to, pressure filling, vacuum filling, gravity filling (e.g., pouring), and/or the like. It should be noted that filling a volume may refer to filling the volume in its entirety or a portion thereof. In some embodiments, the reservoir body 410 may include a fill line 413 such that the interior volume 412 of the reservoir body 410 may be filled with fluidic media approximately up to the fill line 413. The fill line 413 may correspond, for example, to a specific volume (e.g., 2 ml, 3 ml, etc.) of fluidic media to be contained in the interior volume 412 of the reservoir body 410.

The fill line 413 may be located in the first portion 410a of the reservoir body 410. For example, in the embodiment shown in FIG. 14B, the fill line 413 is located between the perimeter 415 and the port 416 of the reservoir body 410. By filling the interior volume 412 of the reservoir body 410 to the fill line 413, the second portion 410b may be removed while mitigating loss of fluidic media from the interior volume 412 of the reservoir body 410. Returning to FIGS. 13-14D, for example, a reservoir body 410 adapted to contain up to approximately 3 ml of fluidic media and having a fill line 413 corresponding to 2 ml of fluidic media may be filled with approximately 2 ml of fluidic media in a case where the reservoir body 410 is filled to the fill line 413. In further embodiments, the fill line 413 may be sufficiently located from the perimeter 415 to allow for sufficient spacing for placing a plunger head (discussed later) within the reservoir body 410. In other words, the plunger head 420 may be positioned between the perimeter 415 and the fill line 413.

Various embodiments may allow for filling not only the first portion 410a, but also additionally, the interior volume 412 of the reservoir body 410 may be filled substantially in its entirety so that the first portion 410a and the second portion 410b of the reservoir body 410 contain fluidic media. As such, the second portion 410b need not be removed from the reservoir body 410. For example, a reservoir body 410 adapted to contain up to approximately 3 ml of fluidic media may be filled with approximately 3 ml of fluidic media. In further embodiments, the interior volume 412 of the reservoir body 410 may be filled substantially in its entirety, but with sufficient spacing for placing a plunger head (discussed later) within the reservoir body 410. In other words, the plunger head may be positioned between the end 417 and the fluidic media contained in the interior volume 412 of the reservoir 410.

In various embodiments, the interior volume 412 of the reservoir body 410 may be filled in an "aseptic environment." The aseptic environment as it is applied in the pharmaceutical/medical industry may refer to an environment in which assembly of sterilized components and product may be processed in a specialized clean environment. For example, the aseptic environment may be one in which living pathogenic organisms and/or contaminants are absent.

Next in step S306 (e.g., FIG. 14C), a seal member, such as a plunger head 420 may be inserted into the reservoir body 410 to prevent fluidic media from flowing out of the reservoir body 410 or to otherwise seal the interior volume 412 of the reservoir body 410. The plunger head 420 may be positioned to contact fluidic media contained in the interior volume 412 of the reservoir body 410. The plunger head 420 may be inserted through an opening, such as the end 417, which may be the same opening in which fluidic media flowed into the interior volume 412 of the reservoir body 410. In other embodiments, the opening through which the plunger head 420 may be inserted may be different from the opening (e.g., port 416) in which fluidic media flowed into the interior volume 412 of the reservoir body 410.

The plunger head 420 or a portion thereof may be made of Bromobutyl rubber, silicone rubber, or any other suitable material and/or any derivative thereof. The plunger head 420 may be arranged for movement in an axial direction of the reservoir body 410 to expand (e.g., FIG. 7A) or contract (e.g., FIG. 7B) the interior volume 412 of the reservoir body 410. The plunger head 420 may be advanceable within the reservoir body 410 to expel fluidic media contained in the interior volume 412 of the reservoir body 410 out the port 416 of the reservoir body 410.

The plunger head 420 may have a front portion 422 and a rear portion 423. In a case where the plunger head 420 is in the reservoir body 410, the front portion 422 of the plunger head 420 may be in contact with fluidic media contained in the interior volume 412 of the reservoir body 410. In some embodiments, the front portion 422 of the plunger head 420 may comprise a material compatible with fluidic media contained in the interior volume 412 of the reservoir body 410. In such embodiments, any number of the remaining portions of the plunger head 420, such as the rear portion 423 of the plunger head 420, a plunger arm (not shown) for moving the plunger head 420 along the reservoir body 410, or the like may be made of a similar material or of any suitable material, including, but not limited to, materials incompatible with fluidic media contained in the interior volume 412 of the reservoir body 410. The rear portion 423 of the plunger head 420 may be connected or connectable to an end of the plunger arm (not shown) in any suitable manner, such as, but not limited to, an adhesive, friction fitting, laser welding, magnetic coupling, or the like.

The plunger head 420 may be or may include a seal member 424, such as an o-ring or the like. The seal member 424 may be positioned between the reservoir body 410 and a portion of the plunger head 420. For example, the seal member 424 may be located between the front portion 422 and the rear portion 423 of the plunger head 420. A portion of the seal member 424 may be in contact with the reservoir body 410. The interior volume 412 of the reservoir body 410 may be on one side of the seal member 424. The open end 417 may be located on an opposite side of the seal member 424 from the interior volume 412 of the reservoir body 410.

The seal member 424 may be for substantially preventing fluidic media from flowing from the interior volume 412 of the reservoir body 410 past the seal member 424, for example, out the end 417 or, in a case where the second portion 410b is to be later removed, into the second portion 410b. Moreover, the plunger head 420 and/or the seal member 424 may substantially prevent fragments of the second portion 410b from entering the interior volume 412 of the reservoir 410 when the second portion 410b is removed from the reservoir body 410. Similarly, the plunger head 420 and/or the seal member 424 may substantially prevent any contaminants from flowing into the interior volume 412 of the reservoir body 410.

In some embodiments, for example in cases where the second portion 410b is to be removed from the reservoir body, the plunger head 420 may be positioned between the perimeter 415 and the fill line 413 to contact the fluidic media contained in the interior volume 412 of the reservoir at the fill line 413.

In various embodiments, the plunger head 420 may be placed in the reservoir body 420 in an aseptic environment, such as that previously described. This aseptic environment may be the same or different from the aseptic environment of step S306.

In step S308 (e.g., FIG. 14D), the second portion 410b may be removed from the reservoir body 410. For example, this may occur in a case where the interior volume 412 of the reservoir body 410 is filled with fluidic media up to the fill line 413 and the plunger head 420 is inserted into the reservoir body 410 to contact the fluidic media contained in the interior volume 412 of the reservoir body 410. As previously discussed, the second portion 410b may be removed from the reservoir body 410 along the perimeter 415. Accordingly, a reservoir body can be filled with a first amount of fluidic media (e.g., 2 ml) and have any excess material (e.g., second portion 410b) removed to selectively provide a full reservoir body. Such a full reservoir body may have a different total volume of fluidic media than a full reservoir body in which first and second portions were filled and the second portion were not removed.

As discussed above, in some embodiments, the end 415' may be substantially smooth once the second portion 410b is removed. In other embodiments, the end 415' may be polished or otherwise finished to substantially remove any irregularities or protuberances to make the end 415' relatively smooth and/or sufficiently smooth for use by a user-patient for example. In some embodiments, such as in a case where the interior volume is filled substantially in its entirety, there may be no need to remove the second portion 410b from the reservoir body 410.

In some embodiments, the reservoir body 110 containing fluidic media and the plunger head 420 may be removed from the aseptic environment, and then placed in a clean environment, such as that previously described, at which point the second portion 410b may be removed. This may mitigate contaminants (e.g., fragments produced from removing the second portion 410b) from contaminating the aseptic environment.

Accordingly, various embodiments allow a filling mechanism (not shown) to selectively fill reservoir bodies with different volumes of fluidic media with little or no adjustment to the filling mechanism (not shown). As such, the filling mechanism (not shown) may fill the same type of reservoir bodies with a selectable amount of fluidic media. For example, scored 3 ml reservoir bodies can be used with a filling mechanism to fill different reservoir volumes, such as 3 ml and 2 ml. Reservoir bodies for containing 3 ml of fluidic media may be produced according to the steps above (e.g., steps S302-S306). Reservoir bodies for containing 2 ml of fluidic media may be produced similarly to the reservoir bodies for containing 3 ml of fluidic media and may be then processed according to step S308 to remove excess portions (e.g., second portion 410b) of the reservoir bodies.

In various embodiments, the reservoir body 410 may include any number of perimeters 415 and/or fill lines 413 each corresponding to a different fill volume as previously described. As such, the filling mechanism (not shown) may fill the same type of reservoir bodies with a plurality of selectable amounts of fluidic media. Thus in such embodiments, a reservoir body can be selectably filled by a filling mechanism with a plurality of different volumes. Portions of the reservoir body that are not needed (e.g., second portion 410b) may be then removed.

In further embodiments, any of the steps described in the process 200 (refer to FIGS. 7A-12) may be carried out, such as, but not limited to, attaching a plunger arm to the plunger head 420, attaching a reservoir cover or plunger arm casing to the end 415' of the reservoir body 410, attaching drive system components to the plunger arm and/or plunger 420, or the like. In some embodiments, the plunger head 420 may be integrated with drive system components. For example, the plunger head 420 may be integrated with a plunger arm, or the like.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A method of making a system for transferring fluidic media, the method comprising:
    filling an interior volume of a reservoir body with fluidic media in a first type of environment;
    placing a plunger head within the reservoir body in the first type of environment, the plunger head adapted to be moveable in an axial direction within the reservoir body;
    attaching a casing adjacent to at least a portion of the reservoir body in a second type of environment, the casing configured to envelop at least a portion of a plunger arm operatively connected to the plunger head, the casing further configured to allow the plunger arm to move in the axial direction relative to the reservoir body and at least partially within the reservoir body;
    locating the plunger arm at least partially in the casing; and
    operatively connecting the plunger arm to the plunger head after the casing is attached to the reservoir body;
    wherein the first type of environment is an aseptic environment and the second type of environment is not an aseptic environment.

2. The method of claim 1, wherein the aseptic environment is free of at least one of contaminants and pathogens.

3. The method of claim 1, the method further comprising:
    operatively connecting the plunger arm to the plunger head in the second type of environment.

4. The method of claim 1, wherein the plunger arm is operatively connected to the plunger head before the casing is attached to the reservoir body.

5. The method of claim 1, wherein the plunger arm and the plunger head are integral to one another.

6. The method of claim 1, wherein attaching a casing adjacent to at least a portion the reservoir body comprises welding the casing to the reservoir body.

7. The method of claim 6, wherein the casing is laser welded to the reservoir body.

8. The method of claim 1, wherein the reservoir body has an open end; and attaching a casing comprises attaching the casing to the open end of the reservoir body to close the open end of the reservoir body.

9. The method of claim 1, wherein attaching the casing to the open end of the reservoir body comprising fitting the casing to the open end of the reservoir body by friction fit.

10. The method of claim 1, wherein attaching the casing comprising attaching the casing to the reservoir body, the method further comprising connecting the plunger arm to the plunger head after attaching the casing to the reservoir body.

11. The method of claim 1, wherein connecting the plunger arm comprises guiding the plunger arm through the casing.

12. The method of claim 11, wherein guiding the plunger arm through the casing comprises passing a tool through an opening in the casing to move the plunger arm along the plunger arm casing to the plunger head.

13. A method of making a system for transferring fluidic media, the method comprising:
    providing a reservoir body having an interior volume for containing a fluidic media;
    placing the reservoir body in a first environment that is separate from a second environment;
    placing a plunger head within the reservoir body while the reservoir body is in the first environment, the plunger head adapted to be moveable in an axial direction within the reservoir body;
    placing the reservoir body with the plunger head placed therein into the second environment;
    attaching a casing to at least a portion of the reservoir body while the reservoir body is in a second type of environment, the casing enveloping at least a portion of a plunger arm that is connected to the plunger head, the casing further configured to allow the plunger arm to move in the axial direction relative to the reservoir body and the casing; locating the plunger arm at least partially in the casing; and operatively connecting the plunger arm to the plunger head after the casing is attached to the reservoir body; wherein the first environment is more aseptic than the second environment.

14. The method of claim 13, wherein second environment contains more contaminants and pathogens than the first environment.

15. The method of claim 13, wherein the first environment is controlled to be more free of contaminants than the second environment.

16. A system for transferring fluidic media, the system comprising:
    a reservoir body having an interior volume for containing a fluidic media;
    a plunger head installed within the reservoir body while the reservoir body is in the first environment, the plunger head adapted to be moveable in an axial direction within the reservoir body a plunger arm operatively connected to the plunger head;
    a casing attached to at least a portion of the reservoir body after the reservoir body is removed from the first environment and placed in a second type of environment, the casing enveloping at least a portion of a plunger arm that is connected to the plunger head, the casing further configured to allow the plunger arm to move in the axial direction relative to the reservoir body and the casing; wherein the first environment is more aseptic than the second environment.

17. The system of claim 16, wherein the first environment is controlled to be more free of contaminants than the second environment.

18. The system of claim 16, wherein the plunger arm and the plunger head are integral to one another.

* * * * *